(12) United States Patent
Zhu et al.

(10) Patent No.: US 9,895,654 B2
(45) Date of Patent: Feb. 20, 2018

(54) WATER REMOVAL DEVICE, METHOD AND SYSTEM FOR GAS SAMPLING

(71) Applicant: EDAN INSTRUMENTS, INC, Shenzhen, Guangdong Province (CN)

(72) Inventors: Zhenying Zhu, Shenzhen (CN); Lu Chen, Shenzhen (CN)

(73) Assignee: EDAN INSTRUMENTS, INC, Shenzhen, Guangdong (CN)

( * ) Notice: Subject to any disclaimer, the term of this patent is extended or adjusted under 35 U.S.C. 154(b) by 191 days.

(21) Appl. No.: 14/903,059

(22) PCT Filed: May 8, 2014

(86) PCT No.: PCT/CN2014/077057
§ 371 (c)(1),
(2) Date: Jan. 6, 2016

(87) PCT Pub. No.: WO2015/070577
PCT Pub. Date: May 21, 2015

(65) Prior Publication Data
US 2016/0151741 A1   Jun. 2, 2016

(30) Foreign Application Priority Data

Mar. 26, 2014   (CN) .......................... 2014 1 0117583

(51) Int. Cl.
*B01D 53/26*   (2006.01)
*A61B 5/08*   (2006.01)
(Continued)

(52) U.S. Cl.
CPC ............ *B01D 53/268* (2013.01); *A61B 5/082* (2013.01); *A61B 5/087* (2013.01); *A61B 10/00* (2013.01);
(Continued)

(58) Field of Classification Search
CPC . A61B 5/087; A61B 2010/0087; A61B 5/082; A61B 2562/0247; A61B 10/00;
(Continued)

(56) References Cited

U.S. PATENT DOCUMENTS

4,270,564 A * 6/1981 Blackburn ............... A61B 5/08
                                                     128/205.12
4,579,568 A * 4/1986 Ricciardelli ........... B01D 19/00
                                                     128/205.12
(Continued)

*Primary Examiner* — Anthony R Shumate
(74) *Attorney, Agent, or Firm* — JCIPRNET (57) ABSTRACT

The present invention relates to a water removal device, method and system for gas sampling. The water removal device comprises a dehydration cup, a gas chamber, a pressure sensor, a flow sensor, a feedback control unit, a main channel and a sucking pump. The feedback control unit controls the working state of the sucking pump according to monitoring data of the pressure sensor and the flow sensor. The water removal device, method and system for gas sampling have the advantages that a double-channel gas sampling structure is adopted so that liquid water in a gas course can be removed effectively. By the adoption of an atmospheric pressure switch structure, no gas flow will pass through a second channel under normal circumstances, and the utilization of sampled gas is increased.

10 Claims, 4 Drawing Sheets

(51) Int. Cl.
*A61B 5/087* (2006.01)
*A61B 10/00* (2006.01)
*A61M 16/08* (2006.01)

(52) U.S. Cl.
CPC ...... *A61M 16/085* (2014.02); *A61M 16/0808* (2013.01); *B01D 53/26* (2013.01); *A61B 2010/0087* (2013.01); *A61B 2562/0247* (2013.01); *B01D 2259/4533* (2013.01)

(58) Field of Classification Search
CPC .......... B01D 53/268; B01D 2259/4533; B01D 53/26; A61M 16/085; A61M 16/0808
See application file for complete search history.

(56) References Cited

U.S. PATENT DOCUMENTS

| | | | | |
|---|---|---|---|---|
| 5,873,256 | A * | 2/1999 | Denniston | B60H 1/00414 62/244 |
| 8,414,682 | B2 * | 4/2013 | Larsen | A61M 16/0808 55/385.1 |
| 2004/0065450 | A1 * | 4/2004 | Yoshida | A62C 25/00 169/56 |
| 2006/0042632 | A1 * | 3/2006 | Bishop | A61B 5/0836 128/207.18 |
| 2010/0042074 | A1 * | 2/2010 | Weston | A61M 1/0066 604/543 |
| 2010/0152880 | A1 * | 6/2010 | Boyden | A61K 9/0019 700/117 |
| 2011/0127051 | A1 * | 6/2011 | Guse | A62C 5/02 169/46 |
| 2012/0052590 | A1 * | 3/2012 | Von Blumenthal | G01N 1/24 436/164 |
| 2012/0136269 | A1 * | 5/2012 | Weckstrom | A61B 5/083 600/532 |
| 2012/0266888 | A1 * | 10/2012 | Dwyer | A61M 16/0808 128/205.27 |
| 2013/0153038 | A1 * | 6/2013 | Barden | G01M 3/005 137/1 |
| 2014/0261824 | A1 * | 9/2014 | Byers | B24B 57/02 137/896 |
| 2014/0276198 | A1 * | 9/2014 | Dunung | A61B 5/036 600/561 |
| 2014/0364758 | A1 * | 12/2014 | Schindhelm | A61B 5/082 600/531 |
| 2015/0032019 | A1 * | 1/2015 | Acker | A61B 5/082 600/532 |
| 2015/0305670 | A1 * | 10/2015 | Spruit | A46B 15/0036 433/27 |
| 2017/0104426 | A1 * | 4/2017 | Mills | H02N 3/00 |
| 2017/0212530 | A1 * | 7/2017 | Potucek | G05D 7/0629 |
| 2017/0212536 | A1 * | 7/2017 | Potucek | G05D 21/02 |

* cited by examiner

WATER REMOVAL DEVICE, METHOD AND SYSTEM FOR GAS SAMPLING

CROSS REFERENCE TO RELATED APPLICATIONS

The present application is the US national stage of International Patent Application PCT/CN2014/077057 filed on May 8, 2014, which, in turn, claims priority to Chinese Patent Application CN 201410117583.6 filed on Mar. 26, 2014.

FIELD OF THE INVENTION

The present invention relates to the field of medical equipment, in particular to a water removal device, method and system for gas sampling.

BACKGROUND OF THE INVENTION

At present, successive and non-invasive determination of breathing gas of a patient by monitoring instruments has been widely used in clinics. Depending on different gas sampling methods, there are two modes for the monitoring of the breathing gas of a patient, i.e., main-stream and side-stream, and particularly side-stream monitoring is most widely used in clinics. Since gas exhaled by a patient will be cooled in the sampled gas course to condense to small drops, during the gas sampling, and the small drops will follow the sampled gas into the analysis gas chamber due to the absence of any water removal device. Consequently, the precision of measurement is influenced, and the analysis gas chamber is polluted and damaged. Therefore, a rational and effective method should be adopted to remove the liquid water in the gas course.

The existing water removal methods mainly revolve the use of dehydration cups and dehumidification tubs. However, the dehumidification tubs are short in service life and high in price. As a result, water removal methods using dehydration cups are more common. Water removal methods using dehydration cups usually employ a double-gas-course sucking and water removal structure where the sampled breathing gas is divided into two parts inside the water removal device; one part is used for detection after water removal and will pass through the first channel, and the other part is used for assisting in removal of accumulated water in the gas course instead of detection and will pass through the second channel. In order to increase the utilization of the sampled gas, the flow of the second channel should be reduced; however, in order to quicken the removal of the accumulated water in the gas course, the flow of the second channel should be increased. Meanwhile, if the flow of the second channel is too low, due to the tension of water, it is unable to make water fall into the cup. Therefore, a rational and effective water removal method and device are needed.

SUMMARY OF THE INVENTION

In order to solve the problems of the prior art, the present invention provides a water removal device for gas sampling.

The present invention provides a water removal device for gas sampling, including a dehydration cup, a gas chamber, a pressure sensor, a flow sensor, a feedback control unit, a main channel and a sucking pump, the dehydration cup being provided with a first channel and a second channel, one end of the gas chamber being communicated to the first channel while the other end of the gas chamber being communicated to the main channel, the second channel being communicated to the main channel, the pressure sensor, the flow sensor and the sucking pump being mounted in the main channel; the pressure sensor is configured to detect a gas pressure value within the first channel and the second channel, the flow sensor is configured to monitor the total gas flow of the first channel and the second channel in real time, the feedback control unit is connected to the pressure sensor, the flow sensor and the sucking pump, respectively, and the feedback control unit control the working state of the sucking pump according to the monitoring data of the pressure sensor and the flow sensor; and the water removal device further includes a water trap, the dehydration cup is provided with a drain hole, the water tank is mounted below the dehydration cup in a sealed manner, and the drain hole is communicated to the water tank.

As a further improvement of the present invention, the dehydration cup includes an upper lid, a lower lid and a hydrophobic membrane, the upper lid and the lower lid being connected to each other in a sealed manner to form a lid body, the hydrophobic membrane being located between the upper lid and the lower lid, the water tank being mounted below the lower lid in a sealed manner; a gas inlet for the first channel and a gas inlet for the second channel are formed on the upper lid, the gas inlet for the second channel being communicated to the first channel, the second channel gas inlet being communicated to the second channel; a gas inlet for a gas channel, the drain hole and a vent hole are formed on the lower lid, the gas inlet for the gas channel being configured to connect an external gas sampling tube, the vent hole being communicated to the water tank; and the pressure sensor is an absolute pressure sensor.

As a further improvement of the present invention, an upper semicircular groove is formed on the upper lid and a lower semicircular groove is formed on the lower lid, the upper semicircular groove and lower semicircular groove forming a separation channel for guiding the separated gas and liquid.

As a further improvement of the present invention, the gas inlet for the first channel is disposed at one end of the upper semicircular groove, the gas inlet for the gas channel is disposed at one end of the lower semicircular groove, and the drain hole is disposed at the other end of the lower semicircular groove.

As a further improvement of the present invention, the water removal device further includes a gas pressure switch which is mounted at the position of the drain hole and configured to be turned on or off when the difference in gas pressure exceeds a certain threshold, the gas pressure switch enables gas or liquid to flow from the dehydration cup toward the water tank.

As a further improvement of the present invention, the gas pressure switch is a check valve made of silica gel; or, the gas pressure switch includes an elastic cushion, one end of the elastic cushion being mounted on the side of the drain hole and the other end of the elastic cushion being stuck close to the position of the drain hole in virtue of own elasticity so as to cover the drain hole.

The present invention further provides a water removal method for gas sampling, including the following steps:

A. initializing the system, commanding a flow sensor and a pressure sensor to start working, and setting a target flow value for a gas;

B. judging whether the pressure value in the gas course exceeds a threshold according to signals sampled by the pressure sensor, if so, executing step C, and if not, continuously executing step B, where the pressure value is equal to the initial gas pressure value minus the current gas pressure value;

C. controlling the power of the sucking pump to reach a preset value;

D. judging whether the gas flow exceeds a flow threshold within a predetermined time duration according to the flow sensor, if so, executing step E, and if not, closing the sucking pump and/or giving an alarm;

E. controlling the power of the sucking pump to stabilize the sucking rate at a target flow value; and F. returning to execute the step B.

As a further improvement of the present invention, the pressure sensor is an absolute pressure sensor; in the step B, it is judged whether the pressure value in the gas course exceeds the threshold according to the signals sampled by the absolute pressure sensor, if so, the step C is executed, and if not, the sucking rate judgment step is executed; in the sucking rate judgment step, it is judged whether the sucking rate reaches the target flow value first, if so, a gas analysis apparatus is commanded to start working and the step B is executed again, and if not, the step E is executed.

The present invention further provides a water removal system for gas sampling, including:

an initialization unit, configured to initialize the system, a flow sensor and a pressure sensor to start working, and setting a target flow value for a gas;

a pressure sensor judgment unit, configured to judge whether the pressure value in the gas course exceeds a threshold according to signals sampled by the pressure sensor, if so, execute a first control unit, and if not, continue to execute the pressure sensor judgment unit, where the pressure value is equal to the initial gas pressure value minus the current gas pressure value;

the first control unit, configured to control the power of the sucking pump to reach a preset value;

a flow sensor judgment unit, configured to judge whether the gas flow exceeds a flow threshold within a predetermined time duration according to the flow sensor, if so, execute a second control unit, and if not, close the sucking pump and/or give an alarm;

the second control unit, configured to control the power of the sucking pump to stabilize the sucking rate at a target flow value; and a returning unit, configured to return to execute the pressure sensor judgment unit.

As a further improvement of the present invention, the pressure sensor is an absolute pressure sensor; in the pressure sensor judgment unit, it is judged whether the pressure value in the gas course exceeds the threshold according to the signals sampled by the absolute pressure sensor, if so, the first control unit is executed, and if not, the sucking rate judgment step is executed; in the sucking rate judgment step, it is judged whether the sucking rate reaches the target flow value first, if so, a gas analysis apparatus is commanded to start working and the pressure sensor judgment unit is executed again, and if not, the second control unit is executed.

The present invention has the following beneficial effects. The water removal device, method and system for gas sampling provided by the present invention employs a double-channel gas sampling structure so that liquid water in a gas course can be removed effectively. By the adoption of an atmospheric pressure switch structure, no gas flow will pass through a second channel under normal circumstances, and the utilization of sampled gas is increased. An absolute pressure sensor is adopted to detect the gas pressure value in the gas course in order to judge whether the gas course is blocked or not and thus to control the working state of the sucking pump, so that the real-time water removal performance is improved. A single flow sensor is adopted to monitor the total flow of the two channels. A negative feedback control unit is utilized to control the gas sucking of the sucking pump. The number of components is reduced and the cost is saved.

DETAILED DESCRIPTION OF THE PREFERRED EMBODIMENTS

Figure 3:
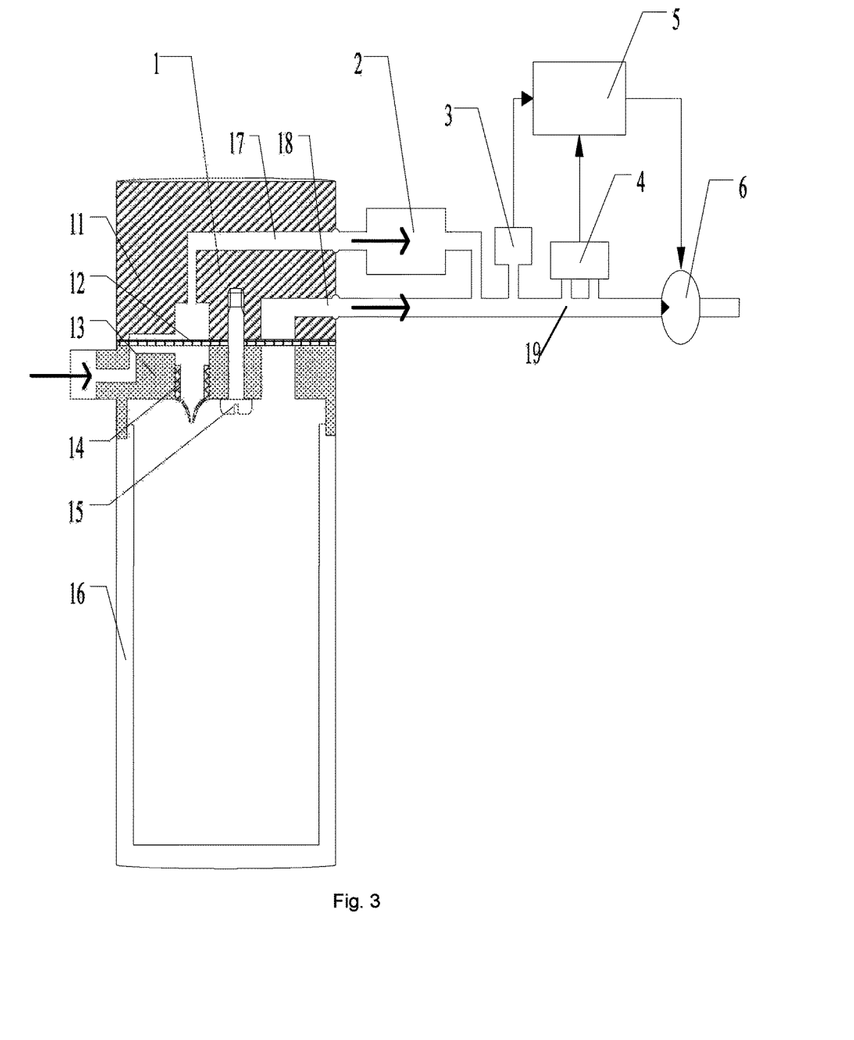
FIG. 3 is a structural principle drawing of a water removal device according to the present invention.

As shown in FIG. 3, the present invention discloses a water removal device for gas sampling, including a dehydration cup 1, a gas chamber 2, a pressure sensor, a flow sensor 4, a feedback control unit 5, a main channel 19 and a sucking pump 6, the dehydration cup 1 being provided with a first channel 17 and a second channel 18, one end of the gas chamber 2 being communicated to the first channel 17 while the other end of the gas chamber 2 being communicated to the main channel 19, the second channel 18 being communicated to the main channel 19, the pressure sensor, the flow sensor 4 and the sucking pump 6 being mounted in the main channel 19; the pressure sensor is configured to detect a gas pressure value within the first channel 17 and the second channel 18, the flow sensor 4 is configured to monitor the total gas flow of the first channel 17 and the second channel 18 in real time, the feedback control unit 5 is connected to the pressure sensor, the flow sensor 4 and the sucking pump 6, respectively, and the feedback control unit 5 control the working state of the sucking pump 6 according to the monitoring data of the pressure sensor and the flow sensor 4; and the water removal device further includes a water tank 16, the dehydration cup 1 is provided with a drain hole 134, the water tank 16 is mounted below the dehydration cup 1 in a sealed manner, and the drain hole 134 is communicated to the water tank 16.

As a preferred embodiment of the present invention, this pressure sensor is an absolute pressure sensor 3. The gas chamber is used for containing gas for detection.

The dehydration cup 1 includes an upper lid 11, a lower lid 13 and a hydrophobic membrane 12, the upper lid 11 and the lower lid 13 being connected to each other in a sealed manner to form a lid body, the hydrophobic membrane 12 being located between the upper lid 11 and the lower lid 13, the water tank 16 being mounted below the lower lid 13 in a sealed manner.

Figure 4:
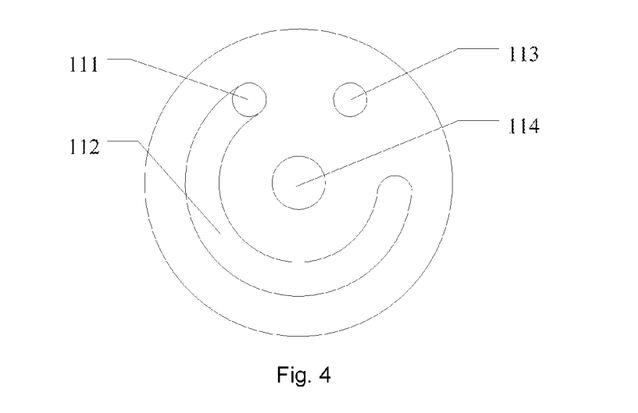
FIG. 4 is a structural diagram of an upper lid according to the present invention.

As shown in FIG. 4, a gas inlet 111 for the first channel and a gas inlet 113 for the second channel are formed on the upper lid 11, the gas inlet 113 for the second channel being communicated to the first channel 17, the second channel gas inlet 113 being communicated to the second channel 18; and this upper lid 11 is further provided with a nut hole 114.

Figure 5:
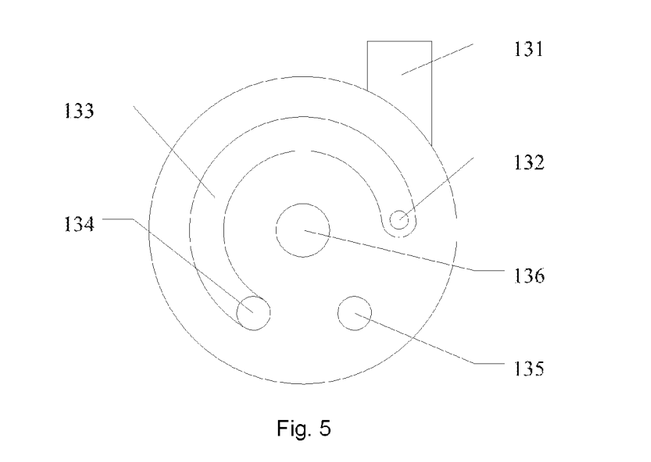
FIG. 5 is a structural diagram of a lower lid according to the present invention.

As shown in FIG. 5, a helical joint 131, a gas inlet 132 for a gas channel, the drain hole 134, a vent hole 135 and a screw via 136 are formed on the lower lid 13, the helical joint 131 being communicated to the gas inlet 132 for the gas channel, the gas inlet 132 for the gas channel being configured to connect an external gas sampling tube; and the drain hole 134 and the vent hole 135 are communicated to the water tank 16.

The hydrophobic membrane 12 allows gas instead of liquid water to pass therethrough, for preventing water in the gas course from entering the first channel 17.

The screw via 136 has a same size and is in a same center line as the nut hole 114 on the upper lid 11 and the screw via of the hydrophobic membrane 12. The lower lid 13 is used in cooperative with the upper lid 11, mainly for providing a gas channel structure and a drain structure for gas sampling.

This water removal device further includes a screw 15 for enabling the upper lid 11, the hydrophobic membrane 12 and the lower lid 13 to closely cooperate with each other. The screw 15 is cooperatively locked to the nut hole 114 on the upper lid 11 after passing through the screw via 136 on the lower lid 13 and then through the hydrophobic membrane 12.

An upper semicircular groove 112 is formed on the upper lid 11 and a lower semicircular groove 133 is formed on the lower lid 13, the upper semicircular groove 112 and lower semicircular groove 133 forming a separation channel. The hydrophobic membrane 12 is used for water-gas separation and the separation channel is used for guiding the separated gas and liquid.

The gas inlet 111 for the first channel is disposed at one end of the upper semicircular groove 112, the gas inlet 132 for the gas channel is disposed at one end of the lower semicircular groove 133, and the drain hole 134 is disposed at the other end of the lower semicircular groove 133. In this way, more gas within the separation channel is guided, and the blind zone is reduced.

The separation channel is preferably C-shaped, because the gas course will become too short if it is linear, and the blind zone of the gas course will be increased if it is N-shaped. In order to improve the efficiency of water-gas separation, the area of the separation channel should be increased, that is, the length of the gas course should be increased. A linear separation channel has a length at most equal to the diameter of the dehydration cup; a C-shaped separation channel is superior to a linear separation channel in terms of length; and with the use of an N-shaped separation channel, there are many turning points in the gas course so that it is likely to cause residual gas and increased blind zone although the length of the channel may be increased.

This water removal device further includes a gas pressure switch 14 which is mounted at the position of the drain hole 134 and configured to be turned on or off when the difference in gas pressure exceeds a certain threshold, the gas pressure switch 14 enables gas or liquid to flow from the dehydration cup 1 toward the water tank 16.

Figure 6:
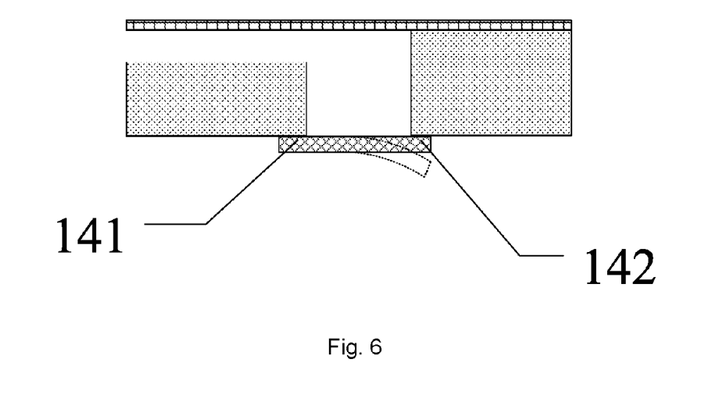
FIG. 6 is a structural diagram of an embodiment of a gas pressure switch according to the present invention.

The gas pressure switch 14 is a check valve made of silica gel; or, as shown in FIG. 6, the gas pressure switch 14 includes an elastic cushion, one end 141 of the elastic cushion being mounted on the side of the drain hole 134 and the other end 142 of the elastic cushion being stuck close to the position of the drain hole 134 in virtue of own elasticity so as to cover the drain hole 134. The other end 142 of the elastic cushion may be opened when the difference in gas pressure on the two sides exceeds a certain threshold, and this elastic cushion is preferably a silica gel pad.

The water tank 16 is made of transparent plastic material so that the water level within the water tank may be seen clearly. The water tank 16 is placed upside down below the lower lid 13, mainly for collecting liquid.

The first channel 17 is from the starting point of the gas inlet 111 for the first channel to the flow sensor 4; and the second channel 18 is from the starting point of the drain hole 134 of the lower lid 13 to the gas pressure switch 14, the water tank 16 and the gas inlet 113 for the second channel and then to the flow sensor 4.

The sampled gas enters the separation channel from the helical joint 131 of the lower lid 13. Due to the presence of the hydrophobic membrane 12 within the separation channel, part of the sampled gas flows into the upper part through the hydrophobic membrane 12 and into the first channel 17. In the case where no water exists in the gas course, a small amount of sampled gas will flow through the gas pressure switch 14 of the second channel 18, to be mixed with the original gas in the water tank 16 and then gathered in the first channel 17 through the hydrophobic membrane 12 and the gas inlet 113 for the second channel. In the case where there is accumulated water in the gas course and normal sucking is performed, due to the tension of the accumulated water, the second channel 18 will be blocked. In the case where there is accumulated water in the gas course and the power of the sucking pump is at a preset value, the negative pressure of the water tank 16 is increased so that the accumulated water may flow into the water tank 16 through the gas pressure switch. The gathered gas then flows through the absolute pressure sensor 3 and the flow sensor 4, and is finally exhausted from the system through the sucking pump 6.

Figure 1:
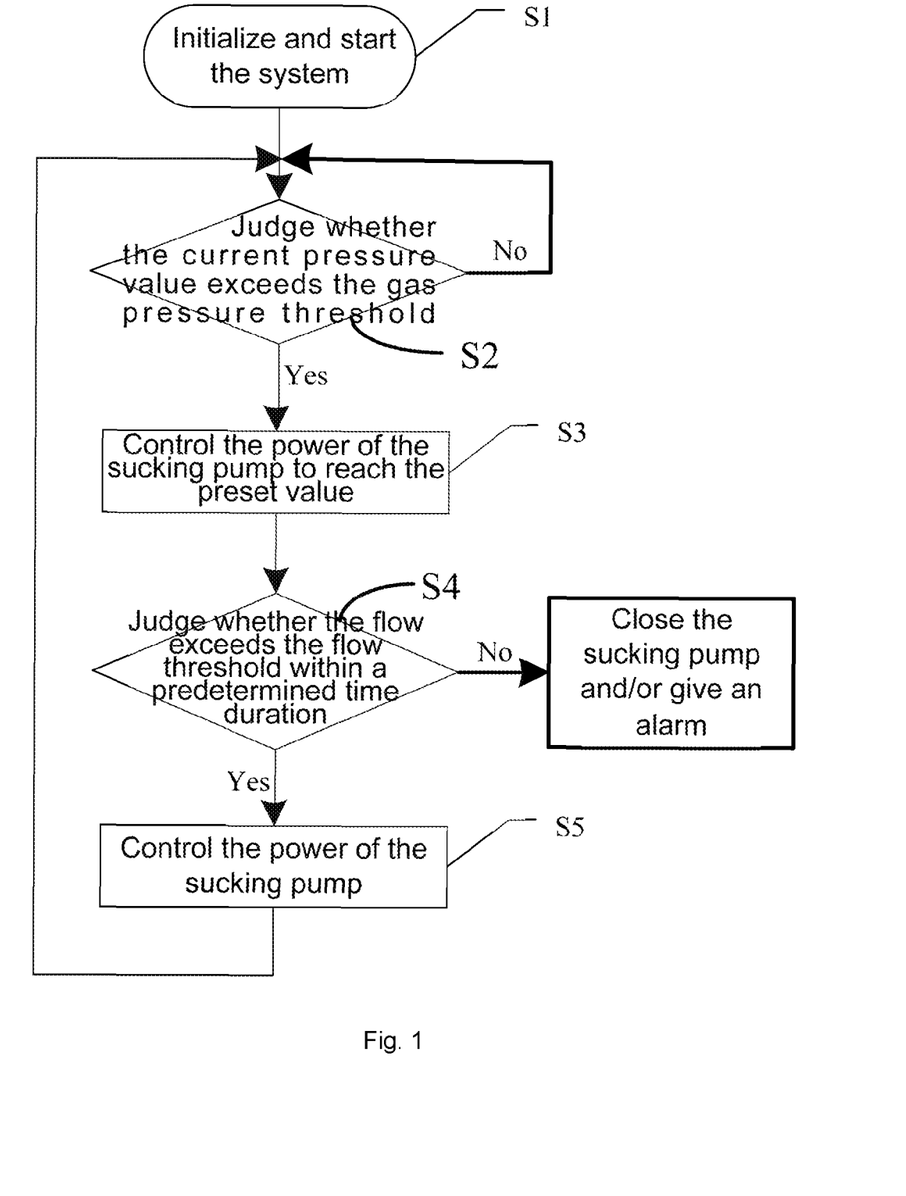
FIG. 1 is a flowchart of a sampling method according to the present invention.

As shown in FIG. 1, the present invention further discloses a water removal method for gas sampling, including the following steps:

in S1: initializing the system, commanding a flow sensor and a pressure sensor to start working, and setting a target flow value for a gas;

in S2: judging whether the pressure value in the gas course exceeds a threshold according to signals sampled by the pressure sensor, if so, executing S3, and if not, continuously executing S2, where the pressure value is equal to the initial gas pressure value minus the current gas pressure value;

in S3: controlling the power of the sucking pump to reach a preset value;

in S4: judging whether the gas flow exceeds a flow threshold within a predetermined time duration according to the flow sensor, if so, executing S5, and if not, closing the sucking pump and/or giving an alarm;

in S5: controlling the power of the sucking pump to stabilize the sucking rate at a target flow value; and in S6: returning to execute S2.

The functions of each of the steps will be described in detail below.

In S1, the system is initialized, the flow sensor and the pressure sensor are enabled to start working, a target flow value is set, and the sucking pump sucks at low power.

In S2, during the continuous sampling of gas, as the exhaled gas has a higher temperature and larger humidity than those of the normal environment, part of moisture in the sampled gas will get cooled and form small drops in the sampling tube. Those small drops will follow the gas flow into the dehydration cup and remain in the gas course below the hydrophobic membrane as they are unable to pass through the hydrophobic membrane in the dehydration cup, and are finally accumulated at the drain hole together with the gas flow. Due to the tension of water and the blockage of the gas pressure switch, the accumulated water is unable to fall into the dehydration cup through the drain hole so that a part of the gas course below the hydrophobic membrane will be blocked. But the unblocked part of the gas course still works and the accumulated water will be increased continuously. Under a constant flow, the negative pressure in the gas course will be increased and the pressure value of the pressure sensor will be decreased. It is judged whether the gas pressure value exceeds a threshold according to the difference of the initial gas pressure value minus the current gas pressure value. If so, the process proceeds to S3.

In S3, if the gas pressure value in the gas course exceeds the threshold, it is indicated that there is too much accumulated water in the gas course and the sucking should be quickened to remove water in the gas course. Therefore, the power of the sucking pump is increased to a preset value, and then the process proceeds to S4.

In S4, when the sucking power reaches the preset value, the negative pressure in the gas course will rise by steps. The negative pressure of the gas course from the accumulated water to the sucking pump will be increased, and due to the effect of a communicating member, the negative pressure of the water tank will also be increased. If the accumulated water in the gas course is forced by the ambient pressure into the water tank through the drain hole and the gas courses in both channels thus become smooth, the flow will exceed a flow threshold; or otherwise, the flow will be below the flow threshold. If the flow exceeds the flow threshold, the process proceeds to S5.

Figure 2:
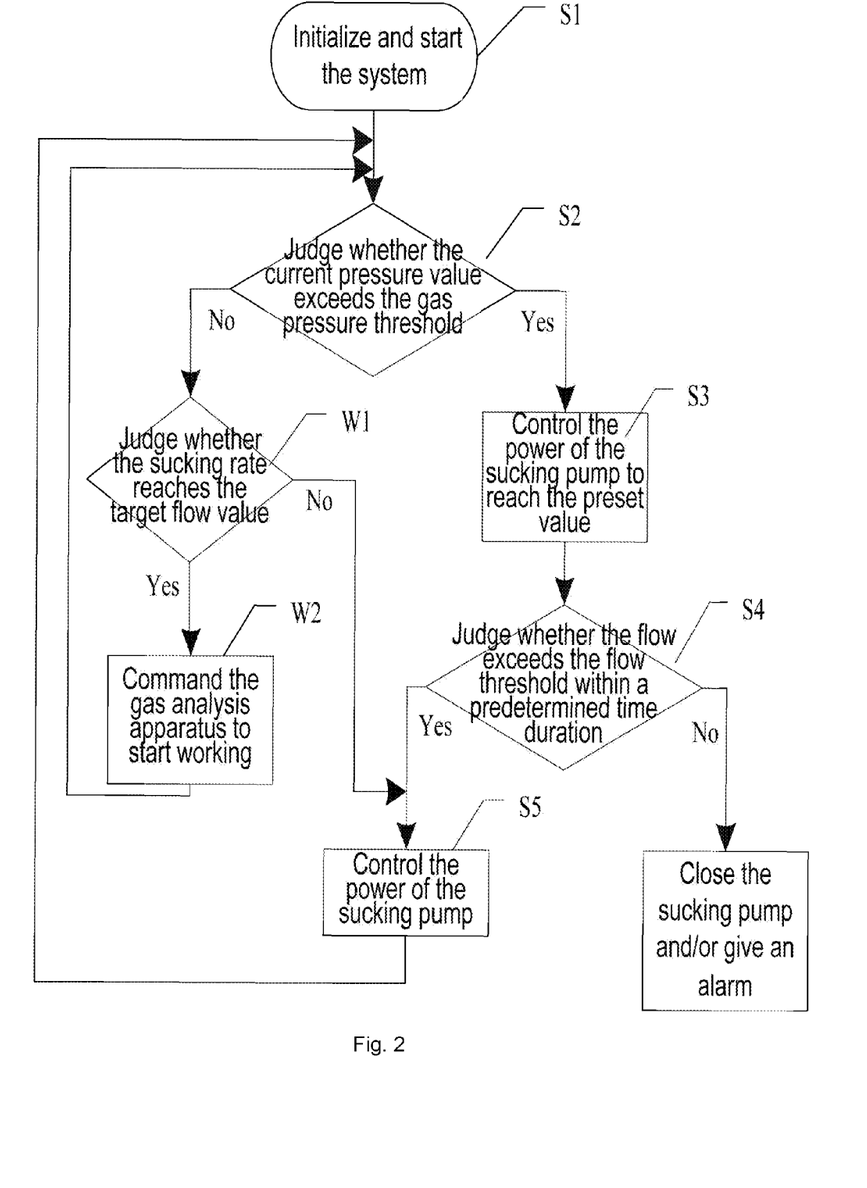
FIG. 2 is a flowchart of an embodiment of the sampling method according to the present invention.

As shown in FIG. 2, as a preferred embodiment of the water removal method of the present invention, the pressure sensor is an absolute pressure sensor. In S2, it is judged whether the pressure value in the gas course exceeds the threshold according to signals sampled by the absolute pressure sensor, if so, S3 is executed; or otherwise, the sucking rate judgment step is executed.

In the sucking rate judgment step, the following steps are included:

In W1, it is judged whether the sucking rate reaches the target flow value, if so, W2 is executed; or otherwise, S5 is executed.

In W2, a gas analysis apparatus is commanded to start working and S2 is executed again.

If the pressure value does not exceed the threshold in S2, it is indicated that there is not too much accumulated water in the gas course, sucking may be performed at the target flow. In this case, W1 is executed.

In W2, gas detection and analysis are carried out. During this process, the accumulated water is still increased. In order to drain the accumulated water in the gas course in time, it is also needed to judge whether the gas pressure value of the gas course is below the gas pressure threshold, so S2 is executed again.

The sucking pump is closed because the dehydration device is full of water or other failures have occurred. In this case, the sucking pump should be closed to ensure the safety of the system.

An alarm is given because the system gives a blockage alarm to the principle computer when it is unable to automatically implement the water removal function.

The present invention further discloses a water removal system for gas sampling, including:

an initialization unit, configured to initialize the system, a flow sensor and a pressure sensor to start working, and setting a target flow value for a gas;

a pressure sensor judgment unit, configured to judge whether the pressure value in the gas course exceeds a threshold according to signals sampled by the pressure sensor, if so, execute a first control unit, and if not, continue to execute the pressure sensor judgment unit;

the first control unit, configured to control the power of the sucking pump to reach a preset value;

a flow sensor judgment unit, configured to judge whether the gas flow exceeds a flow threshold within a predetermined time duration according to the flow sensor, if so, execute a second control unit, and if not, close the sucking pump and/or give an alarm;

the second control unit, configured to control the power of the sucking pump to stabilize the sucking rate at a target flow value; and a returning unit, configured to return to execute the pressure sensor judgment unit.

In the absolute pressure sensor judgment unit, it is judged whether the pressure value in the gas course exceeds the threshold according to signals sampled by the absolute pressure sensor, if so, the first control unit is executed, and if not, the sucking rate judgment module is executed; in the sucking rate judgment module, it is judged whether the sucking rate reaches the target flow value first, if so, a gas analysis apparatus is commanded to start working and the pressure sensor judgment unit is executed again, and if not, the second control unit is executed.

The gas analysis apparatus is configured to perform analysis on a gas, For example, analysis on the exhaled $CO_2$ or $O_2$ or gas exhaled during the anesthesia process can reflect some physiological statuses of a patient.

The water removal device, method and system of the present invention are mainly used in side-stream mode for removal of liquid water in the gas course.

The water removal device, method and system for gas sampling provided by the present invention employs a double-channel gas sampling structure so that liquid water in a gas course can be removed effectively. By the adoption of an atmospheric pressure switch structure, no gas flow will pass through a second channel under normal circumstances, and the utilization of sampled gas is increased. An absolute pressure sensor is adopted to detect the gas pressure value in the gas course in order to judge whether the gas course is blocked or not and thus to control the working state of the sucking pump, so that the real-time water removal performance is improved. A single flow sensor is adopted to monitor the total flow of the two channels. A negative feedback control unit is utilized to control the gas sucking of the sucking pump. The number of components is reduced and the cost is saved.

The foregoing is just further detailed description of the present invention with specific preferred implementations. It should not be considered that the specific implementation of the present invention is limited thereto. For a person of ordinary skill in the art, various simple deductions and replacements may be made without departing from the concept of the present invention, and those deductions and replacements should be regarded as falling into the protection scope of the present invention.

What is claimed is:

1. A water removal device for gas sampling, comprising a dehydration cup, a gas chamber, a pressure sensor, a flow sensor, a feedback control unit, a main channel and a sucking pump, the dehydration cup being provided with a first channel and a second channel, one end of the gas chamber being communicated to the first channel while the other end of the gas chamber being communicated to the main channel, the second channel being communicated to the main channel, and the pressure sensor, the flow sensor and the sucking pump being mounted in the main channel, wherein the pressure sensor is configured to detect a gas pressure value within the first channel and the second channel, the flow sensor is configured to monitor a total gas flow of the first channel and the second channel in real time, the feedback control unit is connected to the pressure sensor, the flow sensor and the sucking pump, respectively, and the feedback control unit controls a working state of the sucking pump according to a monitoring data of the pressure sensor and the flow sensor; and the water removal device further comprises a water tank, the dehydration cup is provided with a drain hole, the water tank is mounted below the dehydration cup in a sealed manner, and the drain hole is communicated to the water tank.

2. The water removal device according to claim 1, wherein the dehydration cup comprises an upper lid, a lower lid and a hydrophobic membrane, the upper lid and the lower lid being connected to each other in a sealed manner to form a lid body, the hydrophobic membrane being located between the upper lid and the lower lid, the water tank being mounted below the lower lid in a sealed manner; a gas inlet for the first channel and a gas inlet for the second channel are formed on the upper lid, the gas inlet for the second channel being communicated to the first channel, the second channel gas inlet being communicated to the second channel; a gas inlet for a gas channel, the drain hole and a vent hole are formed on the lower lid, the gas inlet for the gas channel being configured to connect an external gas sampling tube, the vent hole being communicated to the water tank; and the pressure sensor is an absolute pressure sensor.

3. The water removal device according to claim 2, wherein an upper semicircular groove is formed on the upper lid and a lower semicircular groove is formed on the lower lid, the upper semicircular groove and lower semicircular groove forming a separation channel for guiding a separated gas and a separated liquid.

4. The water removal device according to claim 3, wherein the gas inlet for the first channel is disposed at one end of the upper semicircular groove, the gas inlet for the gas channel is disposed at one end of the lower semicircular groove, and the drain hole is disposed at the other end of the lower semicircular groove.

5. The water removal device according to claim 1, wherein the water removal device further comprises a gas pressure switch which is mounted at a position of the drain hole and configured to be turned on or off when a difference in gas pressure exceeds a certain threshold, the gas pressure switch enables gas or liquid to flow from the dehydration cup toward the water tank.

6. The water removal device according to claim 5, wherein the gas pressure switch is a check valve made of silica gel; or, the gas pressure switch comprises an elastic cushion, one end of the elastic cushion being mounted on the side of the drain hole and the other end of the elastic cushion being stuck close to the position of the drain hole in virtue of its own elasticity so as to cover the drain hole.

7. A water removal method for gas sampling, comprising the following steps:

A) initializing the system, commanding a flow sensor and a pressure sensor to start working, and setting a target flow value for a gas;
B) judging whether a pressure value in a gas course exceeds a threshold according to signals sampled by the pressure sensor, if so, executing step C, and if not, continuously executing step B, where the pressure value is equal to a initial gas pressure value minus a current gas pressure value;
C) controlling a power of a sucking pump to reach a preset value;
D) judging whether a gas flow exceeds a flow threshold within a predetermined time duration according to the flow sensor, if so, executing step E, and if not, closing the sucking pump and/or giving an alarm;
E) controlling the power of the sucking pump to stabilize a sucking rate at the target flow value; and
F) returning to execute the step B.

8. The water removal method for gas sampling according to claim 7, wherein the pressure sensor is an absolute pressure sensor; in the step B, it is judged whether the pressure value in the gas course exceeds the threshold according to the signals sampled by the absolute pressure sensor, if so, the step C is executed, and if not, a sucking rate judgment step is executed; in the sucking rate judgment step, it is judged whether the sucking rate reaches the target flow value first, if so, a gas analysis apparatus is commanded to start working and the step B is executed again, and if not, the step E is executed.

9. A water removal system for gas sampling, comprising:
an initialization unit, configured to initialize the system, a flow sensor and a pressure sensor to start working, and setting a target flow value for a gas;
a pressure sensor judgment unit, configured to judge whether a pressure value in a gas course exceeds a threshold according to signals sampled by the pressure sensor, if so, execute a first control unit, and if not, continue to execute the pressure sensor judgment unit, where the pressure value is equal to a initial gas pressure value minus a current gas pressure value;
the first control unit, configured to control a power of a sucking pump to reach a preset value;
a flow sensor judgment unit, configured to judge whether a gas flow exceeds a flow threshold within a predetermined time duration according to the flow sensor, if so, execute a second control unit, and if not, close the sucking pump and/or give an alarm;
the second control unit, configured to control the power of the sucking pump to stabilize a sucking rate at the target flow value; and
a returning unit, configured to return to execute the pressure sensor judgment unit.

10. The water removal system for gas sampling according to claim 9, wherein the pressure sensor is an absolute pressure sensor; in the pressure sensor judgment unit, it is judged whether the pressure value in the gas course exceeds the threshold according to the signals sampled by the absolute pressure sensor, if so, the first control unit is executed, and if not, a sucking rate judgment module is executed; in the sucking rate judgment module, it is judged whether the sucking rate reaches the target flow value first, if so, a gas analysis apparatus is commanded to start working and the pressure sensor judgment unit is executed again, and if not, the second control unit is executed.

* * * * *